United States Patent [19]

Belleau et al.

[11] 4,428,889

[45] Jan. 31, 1984

[54] P-ALKOXYPHENYLTHIONOPHOSPHINE SULFIDE DIMERS

[75] Inventors: Bernard R. Belleau, Quebec, Canada; Carlo Franchini, Bari, Italy

[73] Assignee: Bristol-Myers Company, New York, N.Y.

[21] Appl. No.: 263,793

[22] Filed: May 14, 1981

[51] Int. Cl.³ .................. C07F 9/40; C07C 103/52
[52] U.S. Cl. .................. 260/927 R; 260/112.5 R; 568/74
[58] Field of Search .................. 260/927 R

[56] References Cited

U.S. PATENT DOCUMENTS 3,711,578  1/1973  Pianka .................. 260/927 R

OTHER PUBLICATIONS

Scheibye et al., "Bull. Soc. Chem. Belg.," vol. 87, (1978), pp. 229–238.
Fritz et al., "Bull. Soc. Chem. Belg.," vol. 87, (1978), pp. 525–534.
Cram, et al., "Organic Chemistry", (1964), p. 361.

Primary Examiner—Anton H. Sutto
Attorney, Agent, or Firm—Richard R. Lloyd

[57] ABSTRACT

Novel p-alkoxyphenylthionophosphine sulfide dimers useful for preparing thiopeptides from peptides.

10 Claims, No Drawings

P-ALKOXYPHENYLTHIONOPHOSPHINE SULFIDE DIMERS

SUMMARY OF THE INVENTION

This invention relates to novel, soluble, dimers of p-alkoxyphenylthionophosphine sulfides having the formula

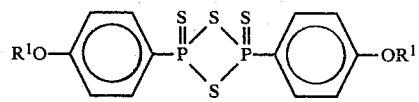
II in which each $R^1$ is the same and is a straight or branched chain alkyl group having from four to six carbon atoms, and to the use of these compounds for converting peptides to thiopeptides.

BACKGROUND AND PRIOR ART (A) Fay and Lankhelma, in J. Am. Chem. Soc., 74, 4933-5 (1952), disclose the reaction of cyclohexene and phosphorus pentasulfide to produce $\Delta^2$-cyclohexenylthionophosphine sulfide, which they propose exists as the dimer having the formula

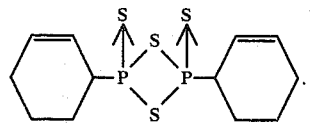

(B) H. Z. Lecher et al., in J. Am. Chem. Soc., 78, 5018-22 (1956), disclose the reaction of phosphorus pentasulfide with benzene, o-xylene, anisole, phenetole, naphthalene and 2-isopropylnaphthalene to form the corresponding dimeric arylthionophosphine sulfides. They are, however, skeptical of the four-membered ring structure proposed by Fay and Lankelma, which would be unique among phosphorus compounds, and suggest that the electrostatic attraction between semipolar P→S bonds causes a bimolecular association in solution, i.e. that the compounds have the following formula

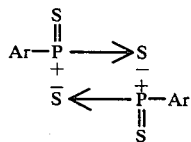

in which Ar is phenyl, o-xylyl, p-methoxyphenyl, p-ethoxyphenyl, 2-naphthyl or 2-isopropyl-X-naphthyl. They state that the very low solubility of these arylthionophosphine sulfides in organic solvents at room temperature also suggests their polar nature. However, regardless of the exact structure, this publication teaches the preparation of two compounds which are closely related to the compounds of Formula II of the present invention, i.e. compounds of Formula II in which $R^1$ is methyl and ethyl rather than a straight or branched chain alkyl group having from four to six carbon atoms, as described and claimed herein.

(C) H. S. Pedersen et al., in Bull. Soc. Chim. Belg., 87, 223-228 (1978), describe the conversion of various ketones, such as benzophenone, 2-benzoylthiophene, dicyclopropyl ketone and camphor, to the corresponding thioketones, using the dimer of p-methoxyphenylthionophosphine sulfide of the formula

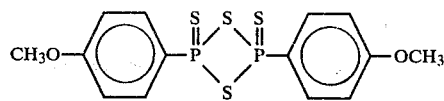

as the thiation reagent. The reaction is conducted in anhydrous toluene at 110° C. until all ketone is consumed (as shown by TLC).

(D) S. Scheibye et al., in Bull. Soc. Chim. Belg., 87, 229-238 (1978), describe the use of the dimer of p-methoxyphenylthionophosphine sulfide as a thiation reagent for converting a representative series of aliphatic and aromatic primary, secondary and tertiary carboxamides to the corresponding thiocarboxamides. They point out that the thiation reagent is quite insoluble in most solvents except in hexamethylphosphoramide (HMPA) at elevated temperatures. Thus, all reactions were conducted in HMPA in the temperature range of 80°-100° C.

(E) S. Scheibye et al., in Bull. Soc. Chim. Belg., 87, 299-306 (1978), describe the use of the dimer of p-methoxyphenylthionophosphine sulfide as a thiation reagent for conversion of secondary o-hydroxybenzamides of the formula

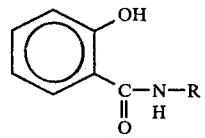

in which R is phenyl, 2,6-dimethylphenyl, benzyl, n-hexyl or cyclohexyl, to the corresponding thioamide. Because of the insolubility of the thiation reagent in most solvents, the reactions were conducted in HMPA, initially at 140° C. and then lowered within 30 minutes to a temperature in the range of 100°-120° C. Yields of desired product were in the range of 15-51%. With the exception of the cyclohexyl compound, where only the desired product was obtained (36%), the reaction gave side products of the formulae

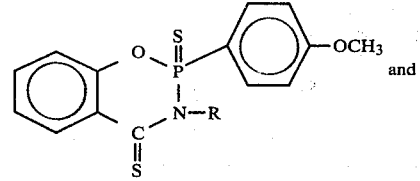
and

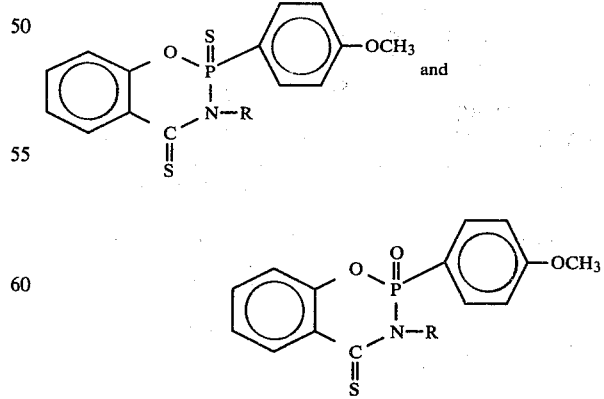

in yields of 5-24% and 13-21%, respectively.

(F) H. Fritz et al., in Bull. Soc. Chim. Belg., 87, 525-534 (1978), describe the use of the dimer of p- methoxyphenylthionophosphine sulfide for the conversion of various N,N-dialkylamides, e.g. those of the formulae

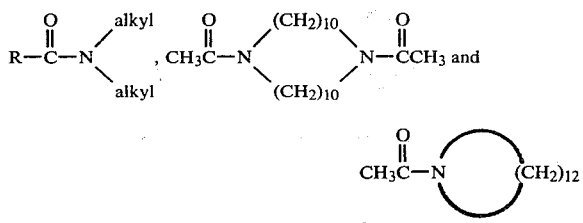

wherein the alkyl groups contain from 1 to 12 carbon atoms and R is hydrogen, methyl, ethyl, propyl, trifluoromethyl, etc., to the corresponding thioamide. The thiation reactions were conducted in anhydrous toluene at a temperature of 100° C.

Complete Disclosure

This application relates to novel, soluble, dimers of p-alkoxyphenylthionophosphine sulfides having the formula

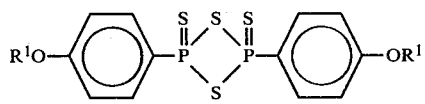

II in which each $R^1$ is the same and is a straight or branched chain alkyl group containing from four to six carbon atoms, and to the use of these compounds as thiation reagents for converting peptides to thiopeptides.

Throughout the specification and claims the structure of the compounds of Formula II will be shown as in the preceding paragraph; but we do not limit ourselves to that specific structure. Thus, it is possible that the compounds of Formula II may, for example, exist, in whole or in part, in the form

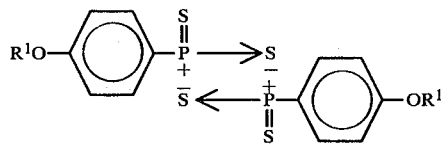

which is not a true dimer but two molecules associated in solution due to electrostatic attraction between semipolar P→S bonds. While of great theoretical interest, the precise structure of the compounds of Formula II is not a necessary or integral part of this invention. It is specifically intended that our representation of the compounds of Formula II as the dimer include the compounds in such alternate forms as that due to bimolecular attraction.

There have been various procedures utilized in the prior art for the conversion of a keto group to a thioketo group, e.g. by reaction with $H_2S$ plus HCl or with $P_2S_5$ plus $NaHCO_3$. But such thiation techniques were usually conducted at high temperature, produced mixtures of products and were not generally applicable. More recently it has been found that the dimer of p-methoxyphenylthionophosphine sulfide is a useful thiation reagent for the conversion of various ketones, esters and amides to the corresponding thioketone, thioester and thioamide. However, this thiation reagent is quite insoluble in organic solvents. It therefore is necessary to conduct the reaction at a temperature in the range of about 100°–140° C. in selected solvents, such as toluene or hexamethylphosphoramide, in order to obtain sufficient solubility of the thiation reagent. Such high reaction temperatures preclude the use of this thiation reagent for the conversion of peptides to thiopeptides, since peptides would be damaged at such high temperatures.

We have now prepared compounds of Formula II wherein $R^1$ is a straight or branched chain butyl, pentyl or hexyl group, and have found them to be surprisingly soluble in common organic solvents, e.g. the compound of Formula II in which $R^1$ is isopentyl is soluble to the extent of approximately 5 g per 100 ml of tetrahydrofuran at about room temperature. The high solubility of these new thiation reagents permits the thiation reaction to be conducted at a sufficiently low temperature for the conversion of peptides to thiopeptides, which was not possible with the prior art p-methoxyphenylthionophosphine dimer. Indeed, we have prepared the p-(n-propyloxy)phenylthionophosphine dimer and found that its solubility in common organic solvents also was too low to be practical for use in the thiation of peptides.

The compounds of Formula II are readily prepared by heating the appropriate alkoxybenzene (I) and phosphorus pentasulfide in a molar ratio of about 10:1, for about 6 hours, at a temperature of about 150° C., under anhydrous conditions. After cooling, an inert organic solvent such as toluene or hexane is added and the reaction mixture is cooled to about 5° C. for about 2 days. The desired product precipitates during this period and is recovered by filtration. The alkoxybenzene starting materials are either commercially available or may readily be prepared by known procedures, e.g. by reacting the appropriate alkyl bromide with phenol and sodium ethoxide. The preparation of the compounds of Formula II is shown in the following Reaction Scheme.

Reaction Scheme I

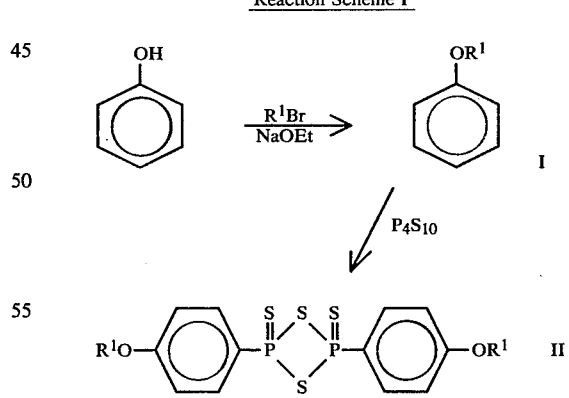

To convert a peptide to a thiopeptide using a thiation reagent of Formula II, one simply stirs a solution of the peptide and the thiation reagent in a dry, aprotic, nonreactive solvent. The reaction may be conducted at a temperature of from about 0° C. to about 60° C., the upper limit of the reaction temperature being dependent on the stability of the peptide or thiopeptide at such temperatures. It is most convenient and economical to conduct the reaction at room temperature, and we therefore prefer to conduct the thiation reaction at ambient temperature. With relatively unreactive peptides, where the reaction would require an inordinate amount of time at room temperature, the reaction may be hastened by conducting it at an elevated temperature, i.e. up to about 60° C., depending on the stability of the peptide and thiopeptide. With extremely reactive peptides, on the other hand, one may slow the reaction by cooling the mixture. We have found that, with some reactive peptides such as t-BOC-glycylglycine methyl ester, the thiation reaction is complete within a few minutes even at 0° C.

The reaction time is not critical and may vary from a few minutes to several days, depending on the reactivity of the peptide and the thiation temperature which is utilized. The course of the reaction may be followed by any of various well-known procedures. We usually prefer to utilize thin layer chromatography (TLC) and continue the reaction until TLC shows that all of the starting peptide has been consumed. As indicated above, the reaction can, if desired, be hastened by heating. Those skilled in the art will appreciate that reaction times at elevated temperatures, e.g. 50°–60° C., should be kept as short as possible if the peptide or thiopeptide is significantly unstable at such temperatures, or if there are substituent groups or protecting groups on the peptide which begin to slowly react with the thiation reagent at such temperatures. In such circumstances, it is normally preferable to conduct the reaction for a longer period at a somewhat lower temperature.

Each molecule of the thiation reagents of Formula II will convert two peptide linkages to thiopeptide linkages. Thus one mole of a dipeptide will require 0.5 mole of the thiation reagent, one mole of a tripeptide will require one mole of the thiation reagent for the conversion of both peptide linkages, one mole of a pentapeptide will require two moles of thiation reagent for the conversion of all four peptide linkages, etc. Because of the high solubility of the thiation reagents of Formula II, it is possible to utilize an excess of the reagent (e.g. 100% excess), if desired, so as to decrease the reaction time. Because of the insolubility of the prior art p-methoxyphenylthionophosphine sulfide dimer, the use of such an excess of reagent was not practical, even at the high temperatures which were utilized (100°–140° C.).

If the peptide starting material contains side chain groups which are reactive with the thiation reagent, the reactive groups should be protected with a suitable protecting (blocking) group before the thiation reaction. Such protecting groups are commonly used in peptide synthesis and are well-known to those skilled in the art. Thus, for example, a carboxyl group on a side chain is readily protected by conversion to an ester, e.g. the methyl ester. Such terminal ester groups are not reactive with the thiation reagents of Formula II. Amino groups may be protected by the tert-butyloxycarbonyl (t-BOC) moiety. Some protecting groups commonly used in peptide synthesis, and which might be present in the peptide molecule undergoing thiation, are themselves slowly reactive with the thiation reagents of Formula II, particularly at elevated temperatures. For example, the t-BOC group is slowly reactive with the thiation reagents of Formula II at temperatures of 50°–60° C. If necessary to conduct the thiation reaction at such temperatures when a t-BOC group is present in the molecule, the reaction time should be as short as possible to avoid extensive degradation of the t-BOC group and the thiation reagent. Preferably, the reaction should be conducted at a lower temperature under such circumstances.

Solvents useful with the thiation reagents of Formula II are those which are aprotic and which do not contain moieties which would react with the thiation reagent. Such solvents will be readily apparent to those skilled in the art, and include benzene, toluene, xylene, tetrahydrofuran, dioxane, methylene chloride, chloroform, carbon tetrachloride, acetonitrile and the like. Solvents containing amide groups, such as N,N-dimethylformamide and N,N-dimethylacetamide, are not suitable for use in the thiation reaction, since they will themselves react with the thiation reagent and be converted into the corresponding thioamides.

It will be appreciated by those skilled in the art that the thiation reagents of Formula II are also useful for converting simple, non-peptide amides to their corresponding thioamides. They will do this in a more efficient manner than the prior art p-methoxyphenylthionophosphine sulfide dimer, because of their much greater solubility. However, the new compounds are particularly useful in the thiation of peptides, since this could not be accomplished with the prior art compound.

EXAMPLE 1

Dimer of p-(n-Pentyloxy)phenylthionophosphine Sulfide (IIa)

(A) n-Pentyloxybenzene (Ia)

Phenol (0.5 mole) was added to a solution of sodium ethoxide in ethanol (2 N; 250 ml) and 1-bromopentane (0.5 mole) was added dropwise while stirring. The mixture was heated under reflux for three hours and most of the solvent was then distilled off. Water was added to the residue and the organic layer was separated, washed twice with 10% aqueous NaOH, water, dilute $H_2SO_4$ and water, and was then dried over $MgSO_4$. It was distilled in vacuo to give the title compound, b.p. 97°–101° C. at 14 mm Hg pressure. The identity and purity was confirmed by thin layer chromatography (TLC) and NMR and IR spectroscopy.

(B) Dimer of p-(n-Pentyloxy)phenylthionophosphine Sulfide (IIa)

n-Pentyloxybenzene (Ia) and $P_4S_{10}$ (in a molar ratio of 10:1) were stirred for six hours at 150° C. under anhydrous conditions. The mixture was cooled, toluene was added, and the reaction flask was left for two days at 5° C. The resulting precipitate was recovered by filtration, washed with anhydrous ether and dried. The yield of product was 46% of theory; after recrystallization from chloroform/petroleum ether it melted at 144°–6° C. Its solubility in tetrahydrofuran was found to be 5 gms/100 ml at room temperature.

Anal. Calc'd for $C_{22}H_{30}O_2P_2S_4$: C, 51.14; H, 5.85; S, 24.82. Found: C, 51.24; H, 5.94; S, 24.67.

NMR (CDCl$_3$), δ values (relative to TMS): 1.14 (6H, $\underline{CH_3}CH_2$—), 1.60 (8H, m, —$\underline{CH_2}CH_3$), 2.03 (4H, m, O$CH_2\underline{CH_2}$R), 4.24 (4H, t, O$\underline{CH_2}CH_2$R), 7.24 (4H, aromatic), 8.64 (4H, aromatic).

Mass Spectrum: M+/2 (m/e)=258

EXAMPLE 2

Dimer of p-(iso-Pentyloxy)phenylthionophosphine Sulfide (IIb)

(A) iso-Pentyloxybenzene (Ib)

Phenol (0.5 mole) was added to a solution of sodium ethoxide in ethanol (2 N; 250 ml) and 1-bromo-3-methylbutane (0.5 mole) was added dropwise while stirring. The mixture was heated under reflux for three hours and most of the solvent was then distilled off. Water was added to the residue and the organic layer was separated, washed twice with 10% aqueous NaOH, water, dilute $H_2SO_4$ and water, and was then dried over $MgSO_4$. It was distilled in vacuo to give the title compound, b.p. 89°–92° C. at 14 mm Hg pressure. The identity and purity was confirmed by thin layer chromatography (TLC) and NMR and IR spectroscopy.

(B) Dimer of p-(iso-Pentyloxy)phenylthionophosphine Sulfide (IIb)

iso-Pentyloxybenzene (Ib) and $P_4S_{10}$ (in a molar ratio of 10:1) were stirred for six hours at 150° C. under anhydrous conditions. The mixture was cooled, hexane was added, and the reaction flask was left for two days at 5° C. The resulting precipitate was recovered by filtration, washed with anhydrous hexane and dried. The yield of product was 27% of theory; after recrystallization from chloroform/petroleum ether it melted at 150°–2° C. Its solubility in tetrahydrofuran was found to be 5 gms/100 ml at room temperature.

Anal. Calc'd for $C_{22}H_{30}O_2P_2S_4$: C, 51.14; H, 5.85; S, 24.82. Found: C, 51.11; H, 5.79; S, 24.78.

EXAMPLE 3

Dimer of p-(n-Butyloxy)phenylthionophosphine Sulfide (IIc)

(A) n-Butyloxybenzene (Ic)

Phenol (0.5 mole) was added to a solution of sodium ethoxide in ethanol (2 N; 250 ml) and 1-bromobutane (0.5 mole) was added dropwise while stirring. The mixture was heated under reflux for three hours and most of the solvent was then distilled off. Water was added to the residue and the organic layer was separated, washed twice with 10% aqueous NaOH, water, dilute $H_2SO_4$ and water, and was then dried over $MgSO_4$. It was distilled in vacuo to give the title compound, b.p. 88°–91° C. at 14 mm Hg pressure. The identity and purity was confirmed by thin layer chromatography (TLC) and NMR and IR spectroscopy.

(B) Dimer of p-(n-butyloxy)phenylthionophosphine Sulfide (IIc)

n-Butyloxybenzene (Ic) and $P_4S_{10}$ (in a molar ratio of 10:1) were stirred for six hours at 150° C. under anhydrous conditions. The mixture was cooled, hexane was added, and the reaction flask was left for two days at 5° C. The resulting precipitate was recovered by filtration, washed with anhydrous hexane and dried. The yield of product was 37% of theory; after recrystallization from chloroform/petroleum ether it melted at 142°–4° C. Its solubility in tetrahydrofuran was found to be 5 gms/100 ml at room temperature.

Anal. Calc'd for $C_{20}H_{26}O_2P_2S_4$: C, 49.16; H, 5.36; S, 26.25. Found: C, 49.37; H, 5.49; S, 25.95.

EXAMPLE 4

Preparation of N-Benzyl-Thioacetamide by Thiation of N-Benzylacetamide

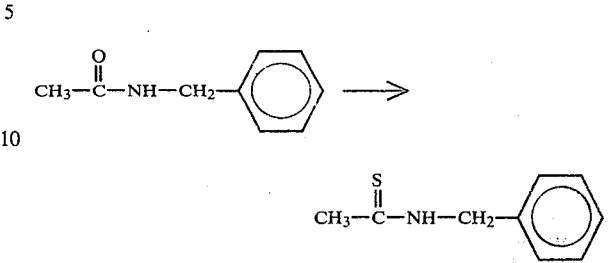

A solution of N-benzyl-acetamide (1.34 mmole, 200 mg) in dry tetrahydrofuran (THF) (5 ml) was stirred with the dimer of p-(n-pentyloxy)phenylthionophosphine sulfide (IIa) (0.67 mmole, 346 mg, molar ratio 1:0.5) under $N_2$ at room temperature. The reaction was followed by TLC (ethyl acetate/petroleum ether 1:2). After 15 minutes no more starting material could be detected. The reaction mixture was poured onto water and the mixture extracted several times with ether. Evaporation of the ether extract left a residue which was purified by chromatography on silica. The benzene-petroleum ether eluate gave pure N-benzylthioacetamide, m.p. 71°–72° (94% yield); NMR ($CDCl_3$), $\delta$ values (relative to TMS): 2.53 (3H, s, $CH_3$); 4.76 (2H, benzylic $CH_2$); 7.28 (5H, aromatic).

The above procedure was repeated except that the dimer of p-(n-pentyloxy)phenylthionophosphine sulfide (IIa) was replaced by the dimers of p-(iso-pentyloxy)-phenylthionophosphine sulfide (IIb) and p-(n-butyloxy)phenylthionophosphine sulfide (IIc), respectively, and N-benzyl-thioacetamide was obtained in each instance in substantially identical yield and purity to that described above.

EXAMPLE 5

Preparation of (+)-N-tert-Butyloxycarbonyl-L-phenyl(thio)alanyl-L-methionine Methyl Ester (IV) by Thiation of (+)-N-tert-Butyloxycarbonyl-L-phenylalanyl-L-methionine Methyl Ester (III)

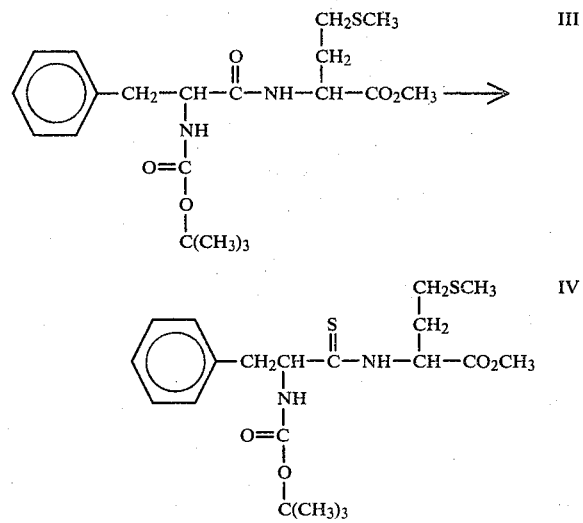

A solution of (+)-N-tert-butyloxycarbonyl-L-phenylalanyl-L-methionine methyl ester (III) (1.7 mmole, 700 mg) in dry THF (10 ml) was stirred in the presence of the dimer of p-(n-pentyloxy)phenylthionophosphine sulfide (IIa) (1.7 mmole, 880 mg) under $N_2$ at room temperature for 24 hours. The reaction was followed by TLC (ethyl acetate/petroleum ether 1:2). The reaction mixture was poured onto water and the mixture extracted three times with $CHCl_3$. The organic residue, after evaporation of the solvent, was purified by chromatography on silica using $CHCl_3$ as the eluent. Fractions 25 to 50 (2 ml each) were pooled and after evaporation of the solvent gave 580 mg (80% yield) of the title thiopeptide (IV) as a colorless syrup; $[\alpha]_D^{24°}$ 50.9 (C=5.35, $CHCl_3$). The $^1H$ NMR ($CDCl_3$) and $^{13}C$ NMR ($CDCl_3$) chemical shifts are given in Table 1, where comparison is made with the spectral properties of the starting dipeptide. The data establish the structure unambiguously.

The above procedure was repeated except that the dimer of p-(n-pentyloxy)phenylthionophosphine sulfide (IIa) was replaced by the dimers of p-(iso-pentyloxy)-phenylthionophosphine sulfide (IIb) and p-(n-butyloxy)phenylthionophosphine sulfide (IIc), respectively, and the thiopeptide IV was obtained in each instance in substantially identical yield and purity to that described above.

EXAMPLE 6

Preparation of N-tert-Butyloxycarbonyl-(thio)glycyl-(thio)glycyl-L-phenylalanine Methyl Ester (VI) by Thiation of N-tert-Butyloxycarbonyl-glycyl-glycyl-L-phenyl alanine Methyl Ester (V)

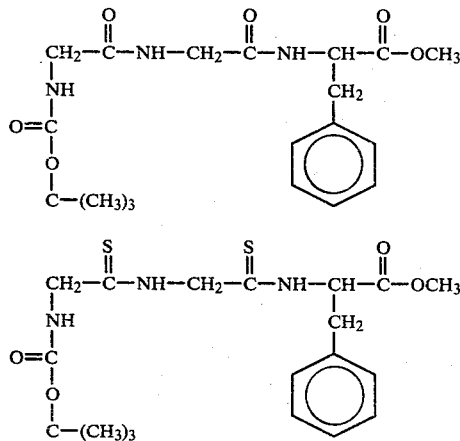

A solution of N-tert-butyloxycarbonyl-glycyl-glycyl-L-phenylalanine methyl ester (V) (2.29 mmole, 900 mg) in dry THF (12 ml) was stirred in the presence of the dimer of p-(n-pentyloxy)phenylthionophosphine sulfide (IIa) (2.75 mmole, 1.42 g, molar ratio 1:1.2) under $N_2$ at room temperature. The reaction was followed by TLC (ethyl acetate/petroleum ether 1:1). After 20 minutes' reaction time two spots (corresponding to the mono- and di-thiation compounds) were detected, with a trace of starting material. After 24 hours of reaction only one spot (the di-thiation compound) was visible. The reaction mixture was then poured onto water and the mixture extracted several times with ether. Evaporation of the ether extract left a residue which was purified by chromatography on silica using $CHCl_3$ as the eluent. There was obtained 890 mg of VI as a colorless oil (90% yield).

The $H^1$ NMR ($CDCl_3$) and $^{13}C$ NMR ($CDCl_3$) chemical shifts are given in Table 2, where comparison is made with the spectral properties of the starting tripeptide. The data establish the structure unambiguously.

It will be appreciated by those skilled in the art that the novel thiation reagents of Formula II, other than those specifically exemplified in Examples 1–3, may be readily prepared by following the procedures set forth above. Thus, by following the general procedure of Example 1, Step B, but replacing the n-pentyloxybenzene used therein by equimolar amounts of
iso-butyloxybenzene,
tert-butyloxybenzene,
sec-butyloxybenzene,
pent-2-yloxybenzene,
n-hexyloxybenzene,
hex-2-yloxybenzene,
hex-3-yloxybenzene,
iso-hexyloxybenzene,
(2-methylpent-2-yloxy)benzene,
(3-methylpent-3-yloxy)benzene and
(2-ethylbut-1-yloxy)benzene, respectively,
there will be obtained
p-(iso-butyloxy)phenylthionophosphine sulfide dimer,
p-(tert-butyloxy)phenylthionophosphine sulfide dimer,
p-(sec-butyloxy)phenylthionophosphine sulfide dimer,
p-(pent-2-yloxy)phenylthionophosphine sulfide dimer,
p-(n-hexyloxy)phenylthionophosphine sulfide dimer,
p-(hex-2-yloxy)phenylthionophosphine sulfide dimer,
p-(hex-3-yloxy)phenylthionophosphine sulfide dimer,
p-(iso-hexyloxy)phenylthionophosphine sulfide dimer,
p-(2-methylpent-2-yloxy)phenylthionophosphine sulfide dimer,
p-(3-methylpent-3-yloxy)phenylthionophosphine sulfide dimer and
p-(2-ethylbut-1-yloxy)phenylthionophosphine sulfide dimer,
respectively.

Similarly, although Examples 4–6 emphasize the use of the preferred thiation reagent p-(n-pentyloxy)phenylthionophosphine sulfide dimer (IIa), other thiation reagents of Formula II may be similarly utilized for the thiation of peptides by following the procedures set forth above. Thus, by following the general procedure of Example 5, but replacing the p-(n-pentyloxy)phenylthionophosphine sulfide dimer used therein by
p-(iso-butyloxy)phenylthionophosphine sulfide dimer,
p-(tert-butyloxy)phenylthionophosphine sulfide dimer,
p-(sec-butyloxy)phenylthionophosphine sulfide dimer,
p-(pent-2-yloxy)phenylthionophosphine sulfide dimer,
p-(n-hexyloxy)phenylthionophosphine sulfide dimer,
p-(hex-2-yloxy)phenylthionophosphine sulfide dimer,
p-(hex-3-yloxy)phenylthionophosphine sulfide dimer,
p-(iso-hexyloxy)phenylthionophosphine sulfide dimer,
p-(2-methylpent-2-yloxy)phenylthionophosphine sulfide dimer,
p-(3-methylpent-3-yloxy)phenylthionophosphine sulfide dimer and
p-(2-ethylbut-1-yloxy)phenylthionophosphine sulfide dimer,
respectively,
(+)-N-tert-butyloxycarbonyl-L-phenyl(thio)alanyl-L-methionine methyl ester will be produced in each instance.

TABLE 1

NMR Characteristics of Compounds III and IV

| | $^1H$ | | | $^{13}C$ | | |
|---|---|---|---|---|---|---|
| | Compound III (ppm) | Compound IV (ppm) | Δδ | Compound III (ppm) | Compound IV (ppm) | Δδ |
| Phe | | | | | | |
| α | 4.37 | 4.58 | +0.21 | 51.59 | 56.95 | +5.36 |
| β | 3.07 | 3.16 | +0.09 | 38.05 | 41.60 | +3.55 |
| γ | | | | 136.5 | 135.6 | −0.9 |
| δ | | | | 129.2 | 128.5 | −0.7 |
| ε | 7.30 (arom.) | 7.30 (arom.) | 0 | 129.2 | 128.5 | −0.7 |
| θ | | | | 128.5 | 127.8 | −0.7 |
| C=X | — | — | — | 171.6 (X=O) | 203.0 (X=S) | +31.4 |
| (CH$_3$)$_3$— | 1.34 | 1.35 | 0.01 | 28.18 | 28.45 | +0.27 |
| —C— | — | — | — | 80.13 | 80.40 | +0.27 |
| Met | | | | | | |
| α | 4.64 | 5.08 | +0.44 | 52.13 | 52.78 | +0.65 |
| β | 2.00 | 2.15 | +0.15 | 31.68 | 30.65 | −1.03 |
| γ | 2.36 | 2.34 | −0.02 | 29.74 | 29.77 | +0.03 |
| δ | 2.00 | 2.00 | 0 | 15.23 | 15.64 | +0.41 |
| C=O | — | — | | 171.08 | 170.14 | −0.94 |
| OCH$_3$ | 3.66 | 3.66 | −0.02 | 55.96 | 62.97 | +7.01 |

TABLE 2

NMR Characteristics of Compounds V and VI

| | $^1H$ | | $^{13}C$ | |
|---|---|---|---|---|
| | Compound V (ppm) | Compound VI (ppm) | Compound V (ppm) | Compound VI (ppm) |
| Gly$^2$ | | | | |
| α | 3.9 | 4.54 | 44.18 | 52.17 |
| C=X | — | — | 170.14 (X=O) | 196.72 (X=S) |
| Gly$^3$ | | | | |
| α | 3.77 | 4.22 | 42.75 | 54.25 |
| C=X | — | — | 171.83 (X=O) | 199.58 (X=S) |
| Phe$^4$ | | | | |
| α | 4.80 | 5.38 | 52.30 | 52.70 |
| β | 3.06 | 3.31 | 37.75 | 36.19 |
| γ | | | 135.83 | 135.05 |
| δ | | | 129.20 | 129.13 |
| ε | 7.20 (arom.) | 7.20 (arom.) | 128.55 | 128.74 |
| θ | | | 127.05 | 127.44 |
| C=O | — | — | 168.60 | 170.72 |

We claim:

1. A p-alkoxyphenylthionophosphine sulfide dimer of the formula

in which each R$^1$ is the same and is a straight or branched chain alkyl group containing from four to six carbon atoms.

2. A compound of claim 1 wherein each R$^1$ is a straight or branched chain butyl group.

3. A compound of claim 1 wherein each R$^1$ is a straight or branched chain pentyl group.

4. A compound of claim 1 wherein each R$^1$ is a straight or branched chain hexyl group.

5. The compound of claim 2 which is p-(n-butyloxy)-phenylthionophosphine sulfide dimer.

6. The compound of claim 2 which is p-(iso-butyloxy)phenylthionophosphine sulfide dimer.

7. The compound of claim 3 which is p-(n-pentyloxy)phenylthionophosphine sulfide dimer.

8. The compound of claim 3 which is p-(iso-pentyloxy)phenylthionophosphine sulfide dimer.

9. The compound of claim 4 which is p-(n-hexyloxy)-phenylthionophosphine sulfide dimer.

10. The compound of claim 4 which is p-(iso-hexyloxy)phenylthionophosphine sulfide dimer.

* * * * *